United States Patent
Grissom et al.

(10) Patent No.: US 12,053,268 B2
(45) Date of Patent: *Aug. 6, 2024

(54) MAGNETIC PARTICLE IMAGING USING AN ULTRASONIC DRIVING FIELD

(71) Applicant: Vanderbilt University, Nashville, TN (US)

(72) Inventors: William A. Grissom, Nashville, TN (US); Charles F. Caskey, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/382,643

(22) Filed: Oct. 23, 2023

(65) Prior Publication Data

US 2024/0041345 A1 Feb. 8, 2024

Related U.S. Application Data

(63) Continuation of application No. 17/667,497, filed on Feb. 8, 2022, now Pat. No. 11,839,458.

(60) Provisional application No. 63/147,088, filed on Feb. 8, 2021.

(51) Int. Cl.
*A61B 5/0515* (2021.01)
*A61B 5/00* (2006.01)
*A61B 8/08* (2006.01)
*G01S 15/89* (2006.01)

(52) U.S. Cl.
CPC .......... *A61B 5/0515* (2013.01); *A61B 5/0035* (2013.01); *A61B 8/485* (2013.01); *G01S 15/8906* (2013.01); *A61B 2562/0223* (2013.01)

(58) Field of Classification Search
CPC ..... A61B 5/0515; A61B 5/0035; A61B 8/485; A61B 2562/0223; A61B 8/481; G01S 15/8906; G01S 15/899
See application file for complete search history.

(56) References Cited

U.S. PATENT DOCUMENTS

| | | | |
|---|---|---|---|
| 2007/0232909 A1* | 10/2007 | Hughes | B82Y 5/00 600/437 |
| 2008/0045865 A1* | 2/2008 | Kislev | A61B 5/411 601/3 |
| 2009/0043198 A1* | 2/2009 | Milner | A61B 8/0816 600/437 |
| 2011/0306870 A1* | 12/2011 | Kuhn | A61B 5/0515 600/12 |
| 2012/0100079 A1 | 4/2012 | Burdinski et al. | |
| 2013/0345547 A1* | 12/2013 | Vahala | A61N 7/02 600/411 |
| 2019/0064736 A1 | 2/2019 | Ruan et al. | |

(Continued)

OTHER PUBLICATIONS

Hossain et al. Magnetic Nanparticle Density Mapping From the Magnetically Induced Displacement Data: A Simulation Study, BioMedical Engineering OnLine, 2012, pp. 1-13.

*Primary Examiner* — Bo Joseph Peng
(74) *Attorney, Agent, or Firm* — Blank Rome LLP

(57) ABSTRACT

A system and method of magnetic particle imaging (MPI) are disclosed. The system and method use ultrasound to drive magnetic particles (such as nanoparticles) through a magnetic field gradient to generate a signal and map the magnetic particles' distribution or concentration.

20 Claims, 3 Drawing Sheets

(56) References Cited

U.S. PATENT DOCUMENTS

2021/0052330 A1\* 2/2021 Kiselyov .............. A61B 8/5269
2024/0041345 A1\* 2/2024 Grissom ................ A61B 8/485

\* cited by examiner

MAGNETIC PARTICLE IMAGING USING AN ULTRASONIC DRIVING FIELD

CROSS REFERENCE TO RELATED APPLICATION(S)

This application is a continuation of U.S. patent application Ser. No. 17/667,497, filed on Feb. 8, 2022, which claims priority to U.S. provisional patent application No. 63/147,088, filed on Feb. 8, 2021, which is hereby incorporated herein by reference in its entirety.

GOVERNMENT SPONSORSHIP

This invention was made with government support under Grant Nos. R01EB016695 and R21EB024199 awarded by the NIH. The government has certain rights in the invention.

FIELD OF THE INVENTION

Embodiments are in the field of magnetic particle imaging. More particularly, embodiments disclosed herein relate to magnetic particle imaging using an ultrasonic driving field.

BACKGROUND OF THE INVENTION

Magnetic particle imaging (MPI) is an emerging medical imaging technology in which magnetic particles (e.g. super paramagnetic iron oxides or SPIOs) are introduced in the subject/body, where they are distributed by the circulation system and in some cases taken up by, for example, tumors. Then, their distribution is imaged using a combination of two magnetic fields that are applied externally. The first field is spatially-varying (a 'gradient' field) which may be one- or multi-dimensional and contains a 'free-field' point where the field is approximately zero. In that location, the particles experience no field and so are not polarized; outside that location the particles are 'saturated'. Then, a separate (usually spatially uniform) magnetic field is applied, which modulates the field throughout the imaged volume. In the gradient zero-field location, that additional driving field modulates the particle's magnetic moment, and drives it into and out of saturation, while particles outside the free-field region remain saturated. The particle's changing magnetic moment generates its own field which can be detected by a nearby signal pickup loop. In that way, the local concentration of particles is measured. The 'free-field' point can then be steered throughout the body to measure particle concentration.

Conventional MPI has some major weaknesses which the present disclosure addresses. The first is the sophistication of the magnetic fields, which must have very large amplitudes, be time-varying, not couple to each other, and the gradient field must either possess a complicated spatial structure (so that it contains a single 'free-field' location) or it must be rotatable (so that it contains a 'free-field line'). The driving field must be powerful and also time-varying, which requires considerable cooling architecture and electric power. Furthermore, the signal generated by the particles has the same fundamental frequency as the driving magnetic field, and is only generated when the driving field is on, so the signal must be measured simultaneously while transmitting at the same frequency, which poses significant electromagnetic and electronic isolation challenges. In practice, since the driving field signal is so large, even with isolation efforts (>100 dB), the signal can only be measured at harmonics of the driving frequency which have much lower amplitudes than the fundamental. Due to the high power requirements for the driving field, it is challenging to mitigate those issues using a spread-spectrum-type encoding. Finally, MPI does not provide a background anatomic image, so it must be spatially registered with separate imaging using a modality such as ultrasound, MRI, or CT.

Thus, it is desirable to provide a system and method for MPI that are able to overcome the above disadvantages.

Advantages of the present invention will become more fully apparent from the detailed description of the invention hereinbelow.

SUMMARY OF THE INVENTION

Embodiments are directed to a method for MPI. The method includes: generating a magnetic field gradient within a subject, wherein magnetic particles embedded in the subject are contained within the magnetic field gradient; generating ultrasound pulses; applying the ultrasound pulses to move the magnetic particles along the magnetic field gradient; detecting magnetic fields produced by the magnetic particles as the magnetic particles' magnetization changes due to the movement of the magnetic particles along the magnetic field gradient; and generating a signal based on the magnetic fields produced in the detecting step.

Embodiments are also directed to a system for MPI. The system includes: gradient coils configured to generate a magnetic field gradient within a subject, wherein magnetic particles embedded in the subject are contained within the magnetic field gradient; an ultrasound transducer that generates ultrasound pulses which are configured to be applied to move the magnetic particles along the magnetic field gradient; a detector coil configured to detect magnetic fields produced by the magnetic particles as the magnetic particles' magnetization changes due to the movement of the magnetic particles along the magnetic field gradient; and a signal generator that generates a signal based on the detected magnetic fields.

Additional embodiments and additional features of embodiments for the method for MPI and system for MPI are described below and are hereby incorporated into this section.

BRIEF DESCRIPTION OF THE DRAWINGS

The foregoing summary, as well as the following detailed description, will be better understood when read in conjunction with the appended drawings. For the purpose of illustration only, there is shown in the drawings certain embodiments. It is understood, however, that the inventive concepts disclosed herein are not limited to the precise arrangements and instrumentalities shown in the figures. The detailed description will refer to the following drawings in which like numerals, where present, refer to like items.

DETAILED DESCRIPTION OF THE INVENTION

Figure 1:
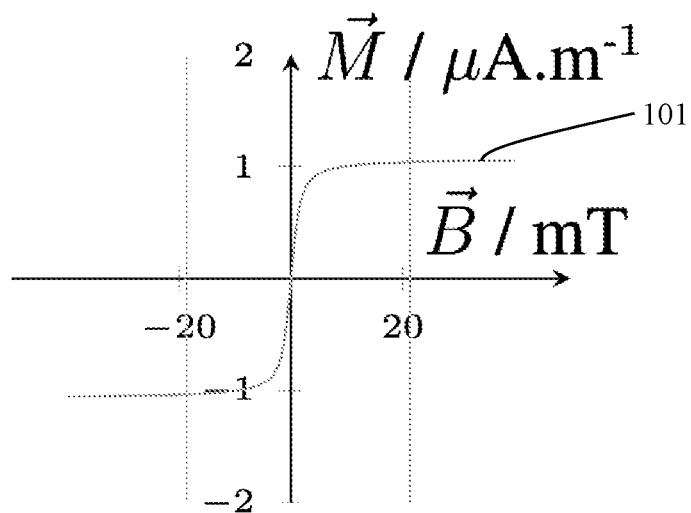
FIG. 1 is a plot illustrating the magnetization of a nanoparticle in response to an externally applied magnetic.

It is to be understood that the figures and descriptions of the present invention may have been simplified to illustrate elements that are relevant for a clear understanding of the present invention, while eliminating, for purposes of clarity, other elements found in a typical MPI device or typical method of using an MPI device. Those of ordinary skill in the art will recognize that other elements may be desirable and/or required in order to implement the present invention. However, because such elements are well known in the art, and because they do not facilitate a better understanding of the present invention, a discussion of such elements is not provided herein. It is also to be understood that the drawings included herewith only provide diagrammatic representations of the presently preferred structures of the present invention and that structures falling within the scope of the present invention may include structures different than those shown in the drawings. Reference will now be made to the drawings wherein like structures are provided with like reference designations.

Before explaining at least one embodiment in detail, it should be understood that the inventive concepts set forth herein are not limited in their application to the construction details or component arrangements set forth in the following description or illustrated in the drawings. It should also be understood that the phraseology and terminology employed herein are merely for descriptive purposes and should not be considered limiting.

It should further be understood that any one of the described features may be used separately or in combination with other features. Other invented devices, systems, methods, features, and advantages will be or become apparent to one with skill in the art upon examining the drawings and the detailed description herein. It is intended that all such additional devices, systems, methods, features, and advantages be protected by the accompanying claims.

A system and method of MPI are disclosed. The system and method use ultrasound to drive magnetic particles (such as nanoparticles) through a magnetic field gradient to generate a signal and map the magnetic particles' distribution or concentration. The particles may label cells or be modified to attach something to them (such as lactoferrin) so that they get taken up by a certain tissue, such as a tumor. In an application, the particles are injected into the body. After some time, they perfuse and are taken up by different organs of interest. And then an image is taken of the distribution or the concentration of the particles.

The present disclosure uses ultrasound or focused ultrasound beams typically used in radiation force imaging to generate a signal from the particles by mechanically pushing them back and forth through a magnetic field gradient. In that way, their magnetic moment will be modulated in a way that can be picked up by the receiver/detector coil, and a signal will only be received from spatial locations which are both in the ultrasound focus, and in a 'free-field' or sufficiently low-field region of the gradient where they are not saturated, but where there exists a sufficient gradient so that the particles' magnetic moment changes as they are moved through the gradient. For example, a single-sided gradient field may be utilized whose amplitude is varied for different depths, without changing its distribution. A linear magnetic field gradient with a free-field line or point can still be used, but when using a gradient with a free-field line, the line need not be rotatable but instead needs only to be translated along the ultrasound axial dimension, since the ultrasound focus can be steered laterally or vertically to different points throughout the zero-field plane. In that way, three-dimensional imaging is possible with a single magnetic field gradient.

An example system to implement this invention would include a Maxwell gradient coil pair placed on either side of the imaging volume, which produces a linear gradient field whose zero point can be translated through the space in-between them by adjusting the relative current in each coil. The ultrasound transducer would be positioned in the middle of one of the coils so that the transducer generates tissue displacement along the magnetic field gradient, which coincides with its axial dimension. A detector coil such as a nearby pickup loop would perform signal detection.

Ultrasound acoustic radiation force (ARF) magnetic particle imaging uses the ARF produced by an ultrasound transducer in tissue to push magnetic particles through a gradient, so that their magnetization (i.e., magnetic moment) changes. If the radiation force is pulsed on and off, the magnetization will change dynamically at the beginning and end of the pulse, which will produce a signal in a nearby receiver coil.

FIG. 1 is a plot 100 illustrating the magnetization of a 30 nm iron nanoparticle in response to an externally applied magnetic field, and is called a Langevin curve 101. Conventional MPI generates signals by oscillating the externally applied magnetic field so that particle magnetization moves along this curve dynamically. The magnetization is purposefully pushed into the flat parts of the curve so that a square-wave magnetization is produced, the time derivative of which (i.e., a train of spikes with alternating signs) can be detected by a receiver coil.

In FIG. 1, the curve 101 comprises a positive flat part and a negative flat part, which are the saturated regions. The curve 101 represents the magnetization of the particles themselves in response to an externally applied magnetic field. The x-axis is the externally applied field that the machine applies.

The free-field point is steered around the body. In the location of the free-field point, a signal from particles can be obtained. Then, a time-varying globally spatially constant field is generated that sums with the background field generated by a set of high-current coils outside the body that's producing the free-field point, and that moves the particles in the free-field point up and down the curve, so that their magnetization is dynamically changing When a receiver coil is placed nearby, the signal can be detected because the changing magnetization in that field is like a generator that generates a signal.

Figure 2:
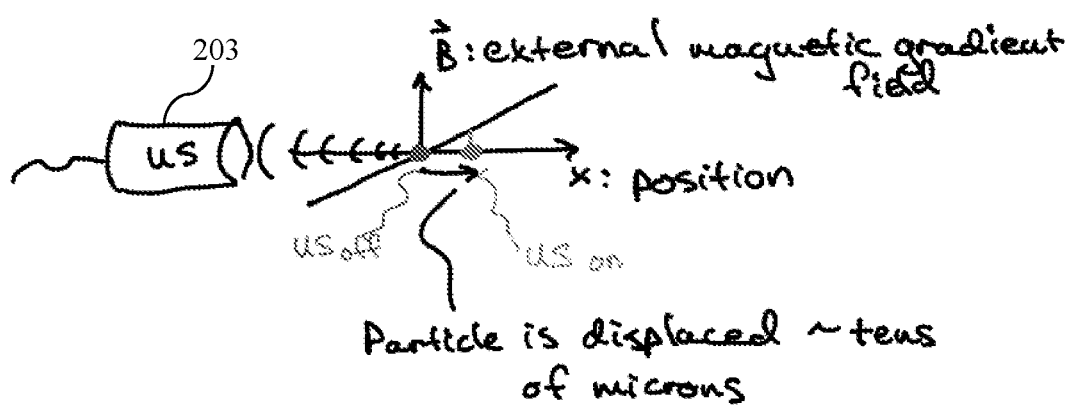
FIG. 2 is a drawing illustrating a schematic view of a system for generating a signal by moving the ultrasound focus around in tissue and pushing the particles themselves to different points in an external magnetic field.

With reference to FIG. 2, instead of moving the free-field point around and applying a time-varying spatially constant field, one can generate a signal via system 200 by moving the ultrasound focus around and pushing the particles themselves to different points in an external magnetic field. So, instead of changing the free-field location, the position of the ultrasound focus is changed in order to move the positions of the particles at each location so they experience a different externally applied field. In system 200, an ultrasound transducer 203 generates an ARF pulse which is able to displace tissue (similar to when performing acoustic radiation force imaging (ARFI)) on the order of up to tens of microns). Essentially, the ultrasound is focused at a location, then the tissue is pushed at that location, and if there are particles at that pushed location (and if we have also created an external magnetic gradient field), then the particles will move along the magnetic field gradient and experience a different magnetic field than when at rest, so they will move to a different point on the curve and their magnetization will change. If that is done repeatedly, the tissue will move back and forth, and a signal is obtained because the particles will be moving up and down the curve. If another coil is placed nearby (such as a loop of wire that is coplanar with the face of the ultrasound transducer, with a magnetic field component parallel to particles' dynamically varying magnetic moment), the particles will generate a signal (a current) in that loop of wire. The invention uses the ARF of ultrasound to displace tissue a small amount, such that if there are particles in that displaced tissue, they will change their magnetization in a dynamic fashion, which will produce a signal. To form an image, the ultrasound focus can be electronically or mechanically steered to a grid of spatial locations, in coordination with movements of the gradient field's free- or low-field region.

Typically, the ultrasound push pulses will be on the order of hundreds of microseconds to several milliseconds. The tissue will displace as represented in the curve shown in FIG. 3A. Assuming the gradients are configured so that particles in the ultrasound focus are in the linear part of the Langevin curve, the signal picked-up in the receiver coil should be a time derivative thereof because the electromotive force in the coil is the time derivative of the changing magnetization. So, with repeated pulses, the signal seen in the coil should be an alternating set of spikes per the plot 302 of FIG. 3C.

To produce an image, one would need to steer the focus of the ultrasound, which is typically done electronically but can also be done mechanically. One may also want to change the strength of the magnetic field as the concentration of the particles is queried at different depths in the tissue. But likely for lateral localization (i.e., lateral to the face of the ultrasound transducer), electronically or mechanically steering the transducer's focus alone would be sufficient.

In an alternative spatial localization method, instead of the steering being performed by the ultrasound, the focus could be elongated (longer than the resolution you actually want in the magnetic particle image). Then, one plays out that focus and moves the free-field point of the gradient field to different points within that focus so that only the signal from that narrower free-field point is obtained. Spatial localization of that signal would depend on both the focus characteristics of the ultrasound and on the characteristics of the gradient (e.g., gradient slope and the position of the free-field point).

In another alternative, a conventional magnetic particle imager that uses coils can be used to move the free-field point around. Then the ultrasound focus can be made to coincide with the free-field point to push particles out of the free-field region, so they develop a magnetic moment and create a signal.

Essentially, ARF is used for displacement of the tissue (or another mechanical motion could alternatively be used such as with an elastography device/driver using repeated palpations) that could push the particles into the free-field region where the particles experience different magnetic fields.

Figure 3A:
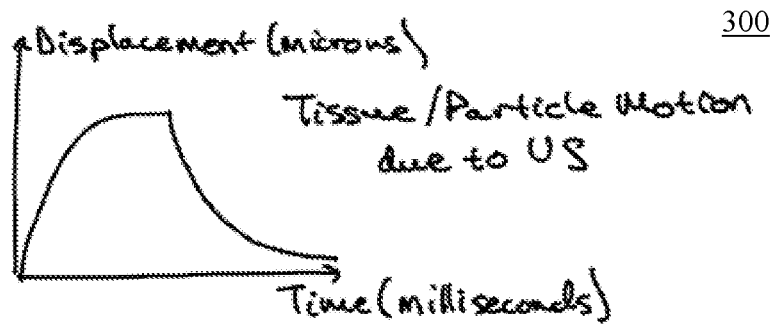
FIGS. 3A-3C are a set of plots respectively illustrating: tissue displacement due to an ARF pulse produced by an ultrasound transducer (FIG. 3A), the change in magnetization due to that displacement (FIG. 3B), and the voltage curve that is produced in a receiver/detector coil by the particles (FIG. 3C)
Figure 3B:
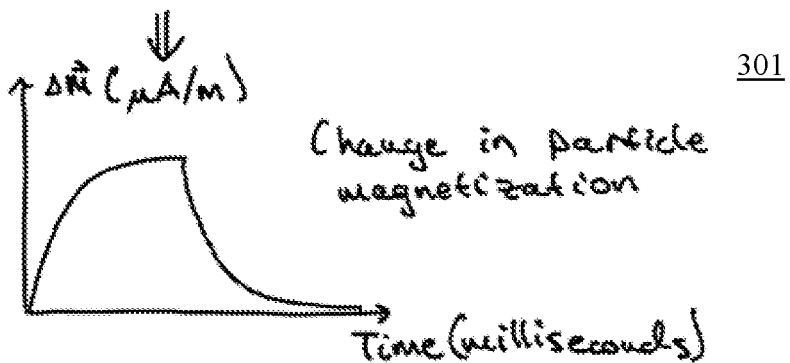

In a most basic implementation of ultrasound-ARF-MPI, the externally applied magnetic field is fixed but spatially varying, and the ARF is used to physically push the particles to a location with differing external magnetic field, thereby changing their magnetization according to a curve similar to the one shown in FIG. 1. Ideally, the magnetization stays within the linear part of the curve, near B=0, to maximize power efficiency. The plot 300 shown in FIG. 3A illustrates tissue displacement due to an ARF pulse produced by an ultrasound transducer (schematically illustrated in FIG. 2) which is typically on the order of tens of microns. The plot 301 shown in FIG. 3B illustrates the change in particle magnetization due to that displacement (assuming that the displacement pushes the particle along the linear part of the Langevin curve). The plot 302 shown in FIG. 3C illustrates the voltage curve that is produced in a receiver coil by the particles.

Note that as long as the magnetic gradient field points along the same direction as the receiver coil's magnetic field, then detection of the changing magnetic field in the particles is possible. The external magnetic field needs to vary spatially in strength along the axial (push) direction of the ultrasound. The vector of that magnetic gradient field has to be parallel to the receiver coil's magnetic field vector, so that the particles' dynamically changing magnetic moments induce a signal in the receiver coil.

Figure 3C:
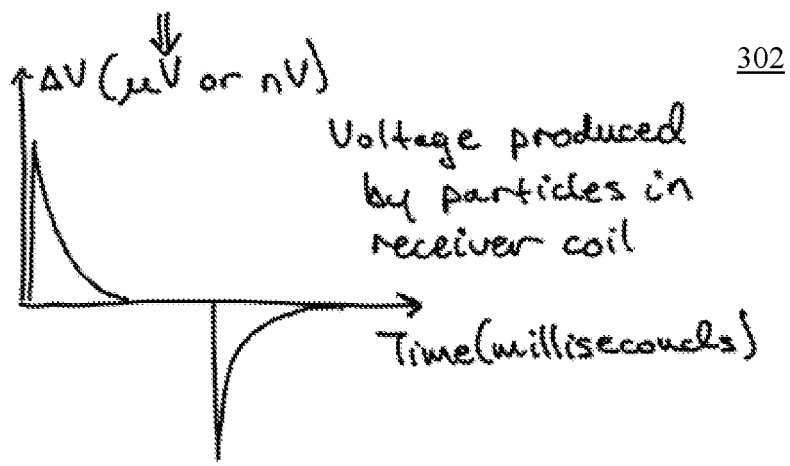

The plots shown in FIGS. 3A-3C also illustrate that the displacement of the particles causes them to experience a different amplitude of the externally applied magnetic field which in turn changes their magnetization according to their Langevin curve. Their change in magnetization then causes a detectable voltage in a receiver coil.

An image of magnetic particle concentration can be formed by electronically steering the ultrasound focus to different points in space, pushing on the tissue at each point, and recording the resulting signal as being proportional to the particle concentration. The external magnetic field is ideally zero at the ultrasound focus location, which can be achieved using conventional gradient coil designs such as with Maxwell pairs. With such gradient coils, the zero or 'free-field' point could be moved to different depths in lockstep with the ultrasound focus by adjusting the relative current amplitude in the different parts of the coils. Lateral signal localization would likely be achieved using ultrasound beam steering alone. A single external field coil could also be used, and its current could be adjusted in lockstep with the ultrasound focal depth, so that the particles at the focus are always in the linear part of the Langevin curve where their magnetization will change with the highest possible slope due to displacement.

Advantages of Embodiments of the Invention

This disclosure has the following advantages over current methods for MPI:
1. Dramatically simplifies system design;
2. Eliminates the simultaneous transmit and receive problem, so that a signal can be measured at the fundamental frequency;
3. Provides accurate spatial localization which is inherently registered with ultrasound anatomic imaging which can be performed with the same ultrasound transducer that generates the driving field. Thus, the ultrasound scanner would be programmed to intermittently collate the data and then the images would be overlaid, thereby providing seamless and efficient registration from a single ultrasound imaging system. Alternatively, different/separate ultrasound transducers may be contemplated;

4. Enables 3D imaging of particle concentration with a single linear gradient. The gradient need not be linear so long as the free-field curve can be moved through the volume approximately along the ultrasound axial dimension;
5. Reduces gradient field strength requirements since particles need not be driven into saturation outside the free-field line; that must be balanced with sensitivity within the free-field region; and
6. Spatial point spread function (a measure of imaging resolution) may likely be better than a typical MPI system, since it will depend on the dimensions of the FUS focus rather than the slope of the gradient field around the free-field line/point.

Additional Description and Observations

SNR may be much lower than conventional MPI due to the lower frequency of the repeated displacements, and the detected signal in the receiver coil is proportional to the time derivative of the particles' magnetic moment. However, MPI SNR is much higher than necessary for signal detection, particles are under development that generate higher signal, and since the driving signal can be controlled by the ultrasound pulse sequence, the opportunity exists to improve the SNR by averaging, spread-spectrum/channel-coding techniques, or lock-in amplifiers to increase sensitivity. One of those SNR improvement techniques may be utilized or the techniques may be complementary in that they could all be applied at once or alone.

The displacement, and consequently the amplitude of the signal, will depend on the tissue stiffness. If necessary, that can be compensated by measuring a map of tissue displacement using, for example, ultrasound ARFI, also with the same (or different) ultrasound imaging transducer. In other words, the measuring of the tissue displacement may be performed using ultrasound imaging methods such as ARFI or ultrasound elastography, to compensate for tissue stiffness in the subject.

Experiment/Example Model

An experimental/model system 400 has been developed to prove a basic premise of this disclosure, i.e., the ARF produced by an ultrasound transducer can push magnetic particles along a magnetic field gradient, thereby dynamically changing magnetic particles' magnetization and producing a signal.

Figure 4:
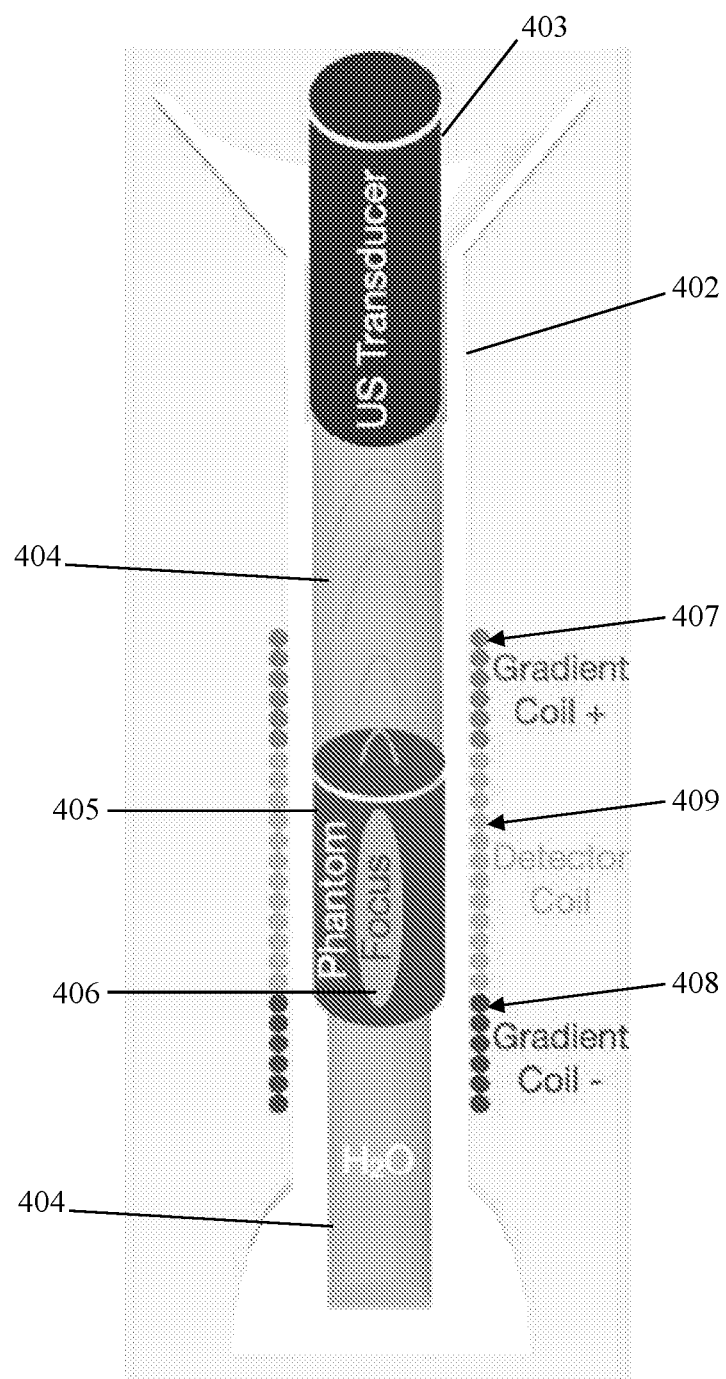
FIG. 4 is a drawing illustrating an experimental system that proves a basic premise of this disclosure, i.e., the ARF produced by an ultrasound transducer can push magnetic particles along a magnetic field gradient, thereby dynamically changing magnetic particles' magnetization and producing a signal.

FIG. 4 shows a cutaway view of the experimental system 400 of a jig 402. The jig 402 is a cylindrical tube which contains water 404 and a gel phantom 405. The phantom 405 comprises, for example, agar, graphite, and magnetic nanoparticles (e.g., VivoTrax, Magnetic Insight). An ultrasound transducer 403 is inserted in the top of the jig so that its focus 406 is centered within the gel phantom 405. With that configuration, the ARF produced by an ultrasound transducer will push particles embedded in the gel phantom 405 downwards (per the orientation depicted in FIG. 4) when the ultrasound is turned on. Three solenoid coils are further wrapped around the outside of the jig. The middle solenoid coil is a receiver/detector coil 409 which is used to sense the magnetic fields produced by the particles as their magnetization changes due to their movement along the magnetic field gradient produced by the upper gradient coil 407 and lower gradient coil 408. The upper and lower gradient coils 407, 408 reflect the opposite direction of electric current running through them, so that they form a Maxwell pair that produces a magnetic field gradient between them. The location in the middle where the magnetic fields cancel is the free-field point. The free-field point is the intersection of the axes shown in the plot portion of FIG. 2.

It was found that the magnitude of the displacements that can be generated feasibly in the body can be quite small in order to generate enough of a magnetic signal which is detectable. The scale of the relevant magnetization would be correspondingly detectable. The free-field region does not need to be wide, so it doesn't take much displacement to push the particles and change their magnetization into and out of the saturation region. The ultrasound is capable of doing that with a feasible amount of electric current running though the gradient coils (less than 10 amps). Moving both the ultrasound focus to different positions and/or changing the strength (and/or direction) of the magnetic field gradient can be used to best align the direction of the ultrasound focus' push with the strongest possible magnetic field gradient in the direction of that push.

In this experiment, the ultrasound transducer is connected to an RF amplifier which is connected to a signal generator, which produces ultrasound pulses of a desired length (hundreds of microseconds to a few milliseconds). The gradient coils 407, 408 are connected to a single power supply that produces several amps of current. The detector coil 409 is connected to an instrumentation amplifier to amplify the signal from the moving particles and is in turn connected to a signal detector, such as an oscilloscope, to record the signal.

The method steps in any of the embodiments described herein are not restricted to being performed in any particular order. Also, structures or systems mentioned in any of the method embodiments may utilize structures or systems mentioned in any of the device/system embodiments. Such structures or systems may be described in detail with respect to the device/system embodiments only but are applicable to any of the method embodiments.

Features in any of the embodiments described in this disclosure may be employed in combination with features in other embodiments described herein, such combinations are considered to be within the spirit and scope of the present invention.

The contemplated modifications and variations specifically mentioned in this disclosure are considered to be within the spirit and scope of the present invention.

More generally, even though the present disclosure and exemplary embodiments are described above with reference to the examples according to the accompanying drawings, it is to be understood that they are not restricted thereto. Rather, it is apparent to those skilled in the art that the disclosed embodiments can be modified in many ways without departing from the scope of the disclosure herein. Moreover, the terms and descriptions used herein are set forth by way of illustration only and are not meant as limitations. Those skilled in the art will recognize that many variations are possible within the spirit and scope of the disclosure as defined in the following claims, and their equivalents, in which all terms are to be understood in their broadest possible sense unless otherwise indicated.

The invention claimed is:

1. A method for magnetic particle imaging (MPI), the method comprising:
generating a magnetic field gradient within a subject;
displacing tissue of the subject along the magnetic field gradient to move magnetic particles within the subject along the magnetic field gradient;
detecting, while displacing the tissue to move the magnetic particles, magnetic fields produced by the magnetic particles; and generating an image based on the magnetic fields detected while displacing the tissue to move the magnetic particles.

2. The method of claim 1, wherein displacing the tissue of the subject along the magnetic field gradient comprises directing palpations at the tissue with an elastography device.

3. The method of claim 1, wherein displacing the tissue of the subject along the magnetic field gradient comprises directing ultrasound pulses at the tissue.

4. The method of claim 3, wherein the ultrasound pulses comprise focused ultrasound beams.

5. The method of claim 3, wherein the ultrasound pulses comprise acoustic radiation force pulses.

6. The method of claim 1, wherein the image is a three-dimensional image.

7. The method of claim 1, further comprising determining a concentration of the magnetic particles.

8. The method of claim 7, wherein determining the concentration of the magnetic particles comprises:
   steering ultrasound beams to different points in space;
   displacing the tissue at each of the different points in space;
   detecting, while displacing the tissue at each of the different points in space, magnetic fields produced by the magnetic particles; and
   determining the concentration of the magnetic particles as proportional to the detected magnetic fields produce by the magnetic particles at the different points in space.

9. The method of claim 1, wherein generating the image based on the magnetic fields detected while displacing the tissue to move the magnetic particles comprises:
   changing a strength of the magnetic field gradient; and
   querying a concentration of the magnetic particles at different depths in the tissue.

10. The method of claim 1, wherein generating the image based on the magnetic fields detected while displacing the tissue to move the magnetic particles comprises mapping a concentration of the magnetic particles.

11. The method of claim 10, wherein mapping of the concentration of the magnetic particles comprises moving foci of ultrasound pulses that displace the tissue to different locations in an image domain.

12. The method of claim 10, wherein mapping of the concentration of the magnetic particles comprises adjusting a strength and an orientation of the magnetic field gradient.

13. The method of claim 10, wherein mapping of the concentration of the magnetic particles comprises:
   moving foci of ultrasound pulses that displace the tissue to different locations in an image domain, and
   adjusting a strength and an orientation of the magnetic field gradient.

14. The method of claim 1, further comprising:
   measuring tissue displacement within the subject; and
   compensating for tissue stiffness in the subject using the measured tissue displacement.

15. The method of claim 14, wherein the measuring of the tissue displacement is performed via ultrasound acoustic radiation force imaging (ARFI) or ultrasound elastography.

16. The method of claim 14, wherein:
   displacing the tissue of the subject along the magnetic field gradient comprises directing ultrasound pulses at the magnetic field gradient, and
   the ultrasound pulses for displacing the tissue and ultrasound pulses for measuring the tissue displacement are produced using a single ultrasound transducer.

17. A system for magnetic particle imaging (MPI), the system comprising:
   gradient coils configured to generate a magnetic field gradient within a subject;
   a device configured to displace tissue of the subject along the magnetic field gradient to move magnetic particles within the subject along the magnetic field gradient;
   a detector coil configured to detect magnetic fields produced by the magnetic particles, while the device displaces the tissue to move the magnetic particles; and
   an imager configured to generate an image based on the magnetic fields detected by the detector coil.

18. The system of claim 17, wherein the device comprises an elastography driver.

19. The system of claim 17, wherein the device comprises an ultrasound transducer.

20. The system of claim 17, wherein the image is a three-dimensional image.

* * * * *